US011801322B2

(12) United States Patent
Grignard, III

(10) Patent No.: US 11,801,322 B2
(45) Date of Patent: Oct. 31, 2023

(54) METHODS OF INACTIVATING PATHOGENS

(71) Applicant: Grignard Pure LLC, Rahway, NJ (US)

(72) Inventor: Emile Etienne Grignard, III, Long Branch, NJ (US)

(73) Assignee: Grignard Pure LLC, Rahway, NJ (US)

( * ) Notice: Subject to any disclaimer, the term of this patent is extended or adjusted under 35 U.S.C. 154(b) by 0 days.

(21) Appl. No.: 17/812,387

(22) Filed: Jul. 13, 2022

(65) Prior Publication Data

US 2023/0041880 A1 Feb. 9, 2023

Related U.S. Application Data

(63) Continuation of application No. PCT/US2022/031908, filed on Jun. 2, 2022.

(60) Provisional application No. 63/226,220, filed on Jul. 28, 2021.

(51) Int. Cl.

| | |
|---|---|
| *A61L 9/00* | (2006.01) |
| *A62B 7/08* | (2006.01) |
| *A61L 9/015* | (2006.01) |
| *A61L 9/02* | (2006.01) |
| *A61L 2/20* | (2006.01) |
| *A61L 9/14* | (2006.01) |
| *A61L 2/22* | (2006.01) |
| *A61L 101/34* | (2006.01) |

(52) U.S. Cl.
CPC .................. *A61L 9/02* (2013.01); *A61L 2/20* (2013.01); *A61L 2/22* (2013.01); *A61L 9/14* (2013.01); *A61L 2101/34* (2020.08); *A61L 2209/21* (2013.01)

(58) Field of Classification Search
CPC ............ B01B 1/005; A61L 9/00; A61L 9/015; A61L 9/02; A61L 9/14; A61L 2209/20; A61L 2209/21
USPC .................... 422/1, 5, 28, 32, 125; 424/76.2
See application file for complete search history.

(56) References Cited

U.S. PATENT DOCUMENTS

| | | | | |
|---|---|---|---|---|
| 2,757,278 A * | 7/1956 | Cloud | A61L 9/03 422/4 |
| 4,748,279 A | 5/1988 | Whiteley | |
| 5,591,395 A | 1/1997 | Schroeder et al. | |
| 7,307,053 B2 | 11/2007 | Tasz et al. | |
| 7,956,026 B2 | 6/2011 | Kobayashi et al. | |
| 9,789,219 B2 | 10/2017 | Kelly et al. | |
| 10,335,508 B2 | 7/2019 | Cosman et al. | |
| 2008/0025942 A1 * | 1/2008 | Weiss | A61L 9/14 424/76.2 |
| 2013/0181013 A1 | 7/2013 | Tasz et al. | |
| 2014/0363333 A1 | 12/2014 | Carr | |
| 2016/0095318 A1 | 4/2016 | Reubens | |
| 2021/0402433 A1 | 12/2021 | Mykytiuk | |
| 2023/0034357 A1 | 2/2023 | Grignard, III | |

FOREIGN PATENT DOCUMENTS

| | | |
|---|---|---|
| CN | 102308790 | 1/2012 |
| CN | 108849891 | 11/2018 |

OTHER PUBLICATIONS

Kethley et al., "A System for the Evaluation of Aerial Disinfectants," Applied and Environmental Microbiology, Sep. 1956, 4(5): 237-243.
Lester et al., "Bactericidal effects of propylene and triethylene glycol vapors on airborne *Escherichia coli*," Science, Apr. 1952, 115(2988):379-382.
Lester et al., "The rate of bactericidal action of triethylene glycol vapor on microorganisms dispersed into the air in small droplets," American Journal of Epidemiology, Sep. 1949, 50(2):175-188.
Potter, "The possibility of prevention of tuberculosis by non-poisonous chemical air disinfection and by killed vaccines," Science, May 1944, 99(2577):406-407.
QBJohnson.com [online], "TEG Dehydrators," available on or before 2006, via Internet Archive: Wayback Machine URL <https://web.archive.org/web/20120513041720/http://www.qbjohnson.com/index5710.html?p=10365>, 4 pages.
Robertson et al., "A study of the bactericidal activity in vitro of certain glycols and closely related compounds," The Journal of Infectious Diseases, Sep.-Oct. 1948, 83(2):124-137.
Robertson, "Disinfection of the air with triethylene glycol vapor," The American Journal of Medicine, Sep. 1949, 7(3):293-296.
SC Johnson, "OUST Aerosol—Clean Scent Ingredients," Product Information Sheet, revised on Apr. 22, 2021, 1 page.

Turgeon et al., "Resistance of Aerosolized Bacterial Viruses to Four Germicidal Products," PLOS One, Dec. 2016, 11(12):e0168815, 1-14.

Bazant et al., "A guideline to limit indoor airborne transmission of Covid-19," Proceedings of the National Academy of Sciences, 2021, 118(17), e201899518, 12 pages.

Chia et al., "Detection of air and surface contamination by SARS-CoV-2 in hospital rooms of infected patients," Nature Communications, 2020, 11(1):1-7.

Department of Health and Human Services, "Guidance for Filtration and Air-Cleaning Systems to Protect Building Environments from Airborne Chemical, Biological or Radiological Attacks," DHHS (NIOSH) Publication No. 2003-136, Apr. 2003, retrieved on Aug. 10, 2022, retrieved from URL <https://www.cdc.gov/niosh/docs/2003-136/pdfs/2003-136.pdf>, 78 pages.

Grignard Pure [online], "Inhalation Exposure to Triethylene Glycol (TEG) in Grignard Pure Products," 2022, retrieved on Aug. 10, 2022, retrieved from URL <https://grignardpure.com/wp-content/uploads/2022/08/TSG-Grignard-Pure-Memorandum_071.22.pdf>, 13 pages.

(Continued)

*Primary Examiner* — Monzer R Chorbaji
(74) *Attorney, Agent, or Firm* — Fish & Richardson P.C.

(57) ABSTRACT

This disclosure relates to a method for sanitizing a space. The method includes applying a composition containing triethylene glycol into a space containing a pathogen (e.g., a *Staphylococcus*, a *Pseudomonas*, a *Listeria, Salmonella, Klebsiella*, a *Mycobacterium*, a mold, or a spore) in an amount effective to inactivate the pathogen.

25 Claims, No Drawings

(56) References Cited

OTHER PUBLICATIONS

Grignard Pure [online], "Tolerable Exposure Derivation for Triethylene Glycol by Inhalation Route and Risk Assessment for Use of Grignard Pure, an antimicrobial air treatment product," Apr. 14, 2022, retrieved on Aug. 10, 2022, retrieved from URL <https://grignardpure.com/wp-content/uploads/2022/08/TSG-Grignard-Pure-Memorandum_071.22.pdf>, 7 pages.

Hamburger et al., "The Effect of Triethylene Glycol Vapor on Air-Borne Beta Hemolytic *Streptococci* in Hospital Wards. I.," The Journal of Infectious Diseases, 1945, 76(3):208-215.

Islam et al., "Current knowledge of Covid-19 and infection prevention and control strategies in healthcare settings: A global analysis," Infection Control and Hospital Epidemiology, 2020, 1-11.

Kaiser., "Provisional Peer-Reviewed Toxicity Values for Triethylene Glycol (CASRN 112-27-6)," United States Environmental Protection Agency, Sep. 10, 2014, 53 pages.

Lambert, "Toxicology Risk Assessment—Grignard Pure," Grignard Company, May 6, 2020, 3 pages.

Liu et al., "Aerodynamic analysis of SARS-CoV-2 in two Wuhan hospitals," Nature, Apr. 2002, 582(7813):557-560.

Rudnick et al., "Inactivating influenza viruses on surfaces using hydrogen peroxide or triethylene glycol at low vapor concentrations," American Journal of Infection Control, Dec. 2009, 37(10):813-819.

Samet et al., "Airborne Transmission of Severe Acute Respiratory Syndrome Coronavirus 2 (SARS-CoV-2): What We Know," Clinical Infectious Diseases: An Official Publication of the Infectious Diseases Society of America, Jan. 2021, 73(10):1924-1926.

Sandars "Reregistration Eligibility Decision (RED) for Triethylene Glycol," Sep. 2003, 74 pages.

U.S Environmental Protection Agency, "Residential Air Cleaners—A Technical Summary," Indoor Environments Division, Jul. 2018, 74 pages.

U.S. Environmental Protection Agency [online], "Aerosol Treatment Technology Evaluation [Reports and Assessments]," Jul. 2021, retrieved on Aug. 10, 2022, retrieved from URL <https://www.epa.gov/covid19-research/aerosol-treatment-technology-evaluation>, 6 pages.

U.S. Environmental Protection Agency [online], "Dipropylene Glycol and Triethylene Glycol; Exemption From the Requirement of a Tolerance," Federal Register, Nov. 3, 2020, 85(213), retrieved on Aug. 10, 2022, retrieved from URL <https://www.federalregister.gov/documents/2020/11/03/2020-23199/dipropylene-glycol-and-triethylene-glycol-exemption-from-the-requirement-of-a-tolerance>, 3 pages.

U.S. Environmental Protection Agency [online], "Emerging Viral Pathogen Guidance and Status for Antimicrobial Pesticides [Other Policies and Guidance]," Apr. 2016, retrieved on Aug. 10, 2022, retrieved from URL <https://www.epa.gov/pesticide-registration/emerging-viral-pathogen-guidance-and-status-antimicrobial-pesticides>, 4 pages.

U.S. Environmental Protection Agency [online], (Sep. 2, 2021b) "Results for Aerosol Treatment Technology Evaluation with Grignard Pure [Reports and Assessments]," Sep. 2, 2021, retrieved on Aug. 10, 2022, retrieved from URL <https://www.epa.gov/covid19-research/results-aerosol-treatment-technology-evaluation-grignard-pure>, 11 pages.

U.S. Environmental Protection Agency, "Guidance to Registrants: Process for Making Claims Against Emerging Viral Pathogens not on EPA-Registered Disinfectant Labels," Aug. 19, 2016, 8 pages.

U.S. Environmental Protection Agency [online], " Disinfectants Pesticides," May 24, 2022, retrieved Aug. 10, 2022, retrieved from URL <https://cfpub.epa.gov/wizards/disinfectants/>, 144 pages.

William et al., "A Comparison of the Grignard Pure Antimicrobial Air Treatment Technology with Enhanced Ventilation and Filtration Strategies for Reducing the Levels of Airborne SARS-CoV-2 Virus Particles," Grignard Pure, 2021, 6 pages.

Zuo et al., "Airborne Transmission of COVID-19: Aerosol Dispersion, Lung Deposition, and Virus-Receptor Interactions," ACS Nano, 2020, 23 pages.

"Summary Review of EPA Office of Research and Development: Homeland Security Research, COVID-19 Research: Ozone and Aerosol Treatment HSRP Webinar Series," 5 pages.

International Search Report and Written Opinion in International Appln. No. PCT/US2022/31908, dated Aug. 24, 2022, 9 pages.

Wikipedia [online], "Methicillin-resistance *Staphylococcus aureus*," Jan. 14, 2022, retrieved on Aug. 29, 2022, retrieved from URL <https://en.wikipedia.org/w/index.php?title=Methicillin-resistant_Staphylococcus_aureus&oldid=1000399800>, 30 pages.

"Coronavirus disease (COVID-19): Similarities and differences with influenza," World Health Organization, Mar. 2020, 4 pages.

"Grignard Pure Atmospherics research documentation for the effectiveness of TEG Vapor for Aerial Disinfection to reduce the spread of air borne viruses and bacteria," Grignard, 2020, 7 pages.

"Summary Review of EPA Office of Research and Development: Homeland Security Research, Covid-19 Research: Ozone and Aerosol Treatment HSRP Webinar Series," 5 pages, Aug. 2021.

"Commercial Exploitation of Glycol Vaporizers," American Journal of Public Health, Feb. 1949, 39(2): 222-224.

Bourouiba, "Turbulent Gas Clouds and Respiratory Pathogen Emissions'—Potential Implications for Reducing Transmission of Covid-19," JAMA Insights, Mar. 2020, E1-E2.

International Search Report and Written Opinion in International Appln. No. PCT/US2021/030881, dated Jul. 13, 2021, 13 pages.

Lester et al., "Factors of Importance in Use of Triethylene Glycol Vapor for Aerial Disinfection," American Journal of Public Health, Jul. 1950, 40: 813-820.

Loosli et al., "Control of Cross-Infections in Infants' Wards by the Use of Triethylene Glycol Vapor," American Journal of Public Health, Nov. 1947, 37: 1385-1398.

Mellody et al., "The fungicidal Action of Triethylene Glycol," J Infect. Dis, Mar. 1946, 79: 45-56.

Puck, "The Mechanism of Aerial Disinfection by Glycols and Other Chemical Agents," The University of Chicago, 1947: 729-739.

Robertson et al., "The Lethal Effect of Triethylene Glycol Vapor on Air-Borne Bacteria and Influenza Virus," Science, Feb. 1943, 97(2510): 142-144.

Robertson, "Sterilization of Air With Glycol Vapors," Harvey Lecture Series, Apr. 1943, 38: 227-254.

Rosebury et al., "Disinfection of Clouds of Meningopneumonitis and Psittacosis Viruses with Triethylene Glycol Vapor," Journal of Exper. Med., 1947, 85: 65-76.

Rudnick et al., "Inactivating Influenza Viruses on Surfaces Using Hydrogen Peroxide or Triethylene Glycol of Law Vapor Concentrations," Federal Aviation Administration, Apr. 2009, 18 pages.

Rutala et al., "Guideline for Disinfection and Sterilization in Healthcare Facilities, 2008" University of North Carolina, May 2019, 163 pages.

Sandle, "Essential Science: Killing Bacteria with new biocide mist," Science, Aug. 2018, 5 pages.

U.S. Department of Homeland Security, "S&T's Research, Development, Testing and Evaluation &RDT&E) Efforts re Covid-19," DHS Science and Technology, Apr. 13, 2020, 16 pages.

United States Environmental Protection Agency, "Efficacy Data and Labeling Requirements: Air Sanitizers," Sep. 5, 2019, 4 pages.

Ward, "Fungicidal effect of triethylene glycol vapor on spores of Penicillium notatum," Retrospective These and Dissertations, 1956, 182 pages.

Office Action in Indian Application No. IN 202217044193, dated Apr. 18, 2023, 6 pages.

\* cited by examiner

METHODS OF INACTIVATING PATHOGENS

CROSS-REFERENCE TO RELATED APPLICATIONS

The present application is a continuation and claims priority to International Application No. PCT/US2022/031908, filed on Jun. 2, 2022, which claims priority to U.S. Provisional Application Ser. No. 63/226,220, filed on Jul. 28, 2021, the contents of which are hereby incorporated by reference in their entirety.

TECHNICAL FIELD

This disclosure relates to compositions and methods for inactivating pathogens in a space (e.g., an indoor space).

BACKGROUND OF THE DISCLOSURE

Human disease is frequently caused by pathogenic microorganisms such as bacteria, viruses, and fungi. The movement of an infectious particle from a host or infected individual to a susceptible new victim can occur by various mechanisms, including breathing of aerosolized fluids from the host, contact with surfaces contaminated by the host or host bodily fluids, or by transfer on the hands of the victim or third party from the host or contaminated surfaces to the victim. The particular transfer mechanism depends on the organism as well as the particular setting. For example, in hospitals and other clinical environments, organisms such as *Enterococcus faecium, Staphylococcus aureus, Klebsiella pneumoniae, Acinetobacter baumannii, Pseudomonas aeruginosa*, and *Enterobacter* species (collectively known as ESKAPE pathogens) and *Clostridium difficile* can cause a significant amount of hospital-acquired infections. Additionally, multi-drug resistant organisms (e.g., MRSA), predominantly bacteria, that are resistant to one or more classes of antimicrobial agents, have special clinical significance because of their acquired resistance. Hospital-acquired infections have become a significant problem for the healthcare industry. As another examination, in the food preparation industry, large-scale food packaging facilities are periodically linked to outbreaks of antibiotic-resistant *Salmonella enterica*, causing numerous deaths. Thus, there is a need for improved methods and compositions for inactivating various pathogens on surfaces or in air in the health care facilities, food packaging facilities, and other settings.

SUMMARY OF THE DISCLOSURE

The inventor has surprisingly found that applying (e.g., by atomizing through an atomizing nozzle or vaporizing through a vapor generating device) a composition containing triethylene glycol (TEG) can effectively inactivate (e.g., kill) various pathogens in the air and/or on the surfaces in an indoor space, thereby effectively sanitizing (e.g., disinfecting or sterilizing) the indoor space (i.e., occupied or unoccupied by human being).

In one aspect, this disclosure features a method for sanitizing a space, the method including applying (e.g., spraying) a composition containing triethylene glycol into a space containing a pathogen in an amount effective to inactivate the pathogen, in which the pathogen includes a *Staphylococcus*, a *Pseudomonas*, a *Listeria*, a *Salmonella*, a *Klebsiella*, a *Mycobacterium*, a mold, or a spore.

Other features, objects, and advantages will be apparent from the description and the claims.

DETAILED DESCRIPTION OF THE DISCLOSURE

As defined herein, unless otherwise noted, all percentages expressed should be understood to be percentages by weight to the total weight of a composition.

In general, this disclosure relates to compositions and methods for sanitizing a space (e.g., an indoor space) by inactivating (or killing) a pathogen in the space. Examples of suitable spaces include those in offices, schools, hotels, lobbies, theaters, reception rooms, bathrooms, health care facilities (e.g., nursing homes, hospital rooms (e.g., intensive care facilities), and medical offices (e.g., dental offices)), food packaging facilities, institutional kitchens, cafeterias, restaurants, public transportation vehicles (buses, trains, subways, and airplanes), ambulances, indoor stadiums and athletic facilities, law enforcement facilities (e.g., prisons), government facilities, elevators, retail locations, and other indoor public or private spaces. In general, the sanitizing composition described herein can be used to inactivate a pathogen either in an unoccupied space (e.g., a space not occupied by human) or an occupied space (e.g., a space occupied by human).

As used herein, the term "inactivating a pathogen" refers to killing a pathogen or otherwise make the pathogen inactive. For example, the sanitizing composition described herein can inactivate viruses, kill bacteria, kill *Mycobacterium*, kill spores, kill mold and mildew.

In some embodiments, the pathogens that can be inactivated by the sanitizing composition described herein can include bacteria (e.g., gram-positive bacteria, gram-negative bacteria, or antibiotic-resistant bacteria), fungi (e.g., molds), viruses (e.g., enveloped viruses or non-enveloped viruses), and spores (e.g., spores produced by fungi or bacteria). Examples of pathogens that can be inactivated by the sanitizing composition described herein include Methicillin-resistant *Staphylococcus aureus* (MRSA; a gram-positive bacterium)), a mold (e.g., an *Aspergillus* such as *Aspergillus brasiliensis*), a *Pseudomonas* (e.g., *Pseudomonas aeruginosa*; a gram-negative bacterium), a *Listeria* (e.g., *Listeria monocytogenes*; a gram-positive bacterium), a *Salmonella* (e.g., *Salmonella enterica*; a gram-negative bacterium), a *Klebsiella* (e.g., *Klebsiella pneumonia*; a gram-negative bacterium), a *Mycobacterium* (e.g., *Mycobacterium tuberculosis*), a spore (e.g., an anthrax spore, a *Clostridium difficile* spore, or a mold spore), or a mixture thereof. Examples of enveloped viruses that can be inactivated by the sanitizing composition described herein include lassa virus, marburg virus, pneumonia, smallpox, croup virus, human parainfluenza viruses (HPIVs), respiratory syncytial virus (RSV), ebola virus, German measles (rubella), herpes simplex (HSV), mumps, Influenza (e.g., H1N1 virus), coronavirus (e.g., SARA-CoV-2 virus), and chickenpox. Examples of non-enveloped viruses that can be inactivated by the sanitizing composition described herein include rhinoviruses, enteroviruses, and parvoviruses.

In some embodiments, this disclosure features a sanitizing composition containing (e.g., comprising, consisting essentially of, or consisting of) triethylene glycol and water (e.g., deionized water). Triethylene glycol is miscible with water, has a boiling point of 286.5° C. at a pressure of 101.325 kPa, and has a relative low vapor pressure compared to water. Without wishing to be bound by theory, it is believed that triethylene glycol inactivates a pathogen by condensing on pathogen-containing particles, droplets, or surfaces until the concentration of triethylene glycol becomes sufficiently high to denature the pathogen. Further, without wishing to be bound by theory, it is believed that triethylene glycol is highly hydroscopic and can inactivate (e.g., kill) a pathogen by absorbing water from the pathogen. In addition, without wishing to be bound by theory, it is believed that triethylene glycol has very low acute or chronic toxicity when inhaled or ingested (especially at the level used in the air to sanitize (e.g., disinfect) an indoor space) and therefore is safe to use in indoor spaces (occupied or unoccupied).

In general, the amount of triethylene glycol in the sanitizing composition described herein is not particular limited and can vary as desired. For example, a sanitizing composition containing a relatively low amount of triethylene glycol can achieve the same disinfection effect as a sanitizing composition containing a relatively high amount of triethylene glycol by applying the former composition in an indoor space at a higher frequency or in a higher amount. In some embodiments, the sanitizing composition described herein can include triethylene glycol in an amount of from at least about 1% (e.g., at least about 5%, at least about 10%, at least about 20%, at least about 30%, at least about 40%, at least about 50%, at least about 52%, at least about 55%, at least about 60%, at least about 65%, at least about 70%, at least about 75%, or at least about 80%) by weight to at most about 99.5% (e.g., at most about 99%, at most about 95%, at most about 90%, at most about 85%, at most about 80%, at most about 75%, at most about 70%, at most about 65%, at most about 60%, or at most about 50%) by weight of the composition. In some embodiments, triethylene glycol can be 100% of the sanitizing composition described herein (i.e., without any other ingredient). It is believed that applying a sanitizing composition containing a relatively high amount (e.g., at least about 50% by weight) of triethylene glycol can increase the efficiency of the disinfection and reduce the frequency of the application of the composition.

In some embodiments, the water in the sanitizing composition described herein is deionized water, reverse osmosis (RO) water, or ultrapure water (e.g., when used in a vaporizer). In some embodiments, the water can have a resistivity of at least 17 mega Ohms, a total organic carbon content of at most about 10 ppb, a bacterial count of at most about 10 CFU/ml). For example, the water can include ions in an amount of from at most about 50 ppm (e.g., at most about 40 ppm, at most about 30 ppm, at most about 20 ppm, at most about 10 ppm, at most about 5 ppm, or at most about 1 ppm) to at least about 1 ppb (e.g., at least about 10 ppb) of the total amount of the water. In some embodiments, when the sanitizing composition described herein is used in connection with an atomizer (e.g., a nebulizer), the water in the composition can be tap water (i.e., not deionized water, RO water, or ultrapure water).

In some embodiments, the sanitizing composition described herein can include water in an amount of from at least about 1% (e.g., at least about 5%, at least about 10%, at least about 15%, at least about 20%, at least about 25%, at least about 30%, at least about 35%, at least about 40%, at least about 45%, at least about 48%, at least about 50%, at least about 60%, or at least about 70%) by weight to at most about 99% (e.g., at most about 95%, at most about 90%, at most about 85%, at most about 80%, at most about 75%, at most about 70%, at most about 65%, at most about 60%, at most about 50%, or at most about 48%) by weight of the composition. Without wishing to be bound by theory, it is believed that using deionized water, RO water, or ultrapure water can minimize clogging the nozzles (e.g., caused by deposition of minerals in water) of the system (e.g., a vaporizer) used to apply the sanitizing composition described herein and therefore can keep the system operating for an extended period of time. In addition, without wishing to be bound by theory, it is believed that the water in the sanitizing composition described herein can facilitate inactivation of pathogens.

Without wishing to be bound by theory, it is believed that including water in the sanitizing composition can allow the composition to be readily nebulized, atomized or vaporized (e.g., by reducing the vaporization temperature and/or increasing the evaporation rate when the sanitizing composition is applied by an atomizer such as a nebulizer, a humidifier, a fog/haze machine, or a smoke generator) and to form an aerosol or vapor in the atmosphere. The water in the aerosol can evaporate rapidly to form fine TEG droplets, which have sanitizing effects and inactivate pathogens in the air or on a surface. In addition, the water in the sanitizing composition can render the composition inflammable, thereby resulting in a safer product than TEG alone (which is a flammable liquid having a flash point of 157° C.).

In some embodiments, the sanitizing composition described herein can further include an optional ingredient, such as a glycol different from triethylene glycol. In some embodiments, the additional glycol can be propylene glycol. Without wishing to be bound by theory, it is believed that the additional glycol can either increase the sanitizing effect of the composition or increase the whiteness of the composition (e.g., to indicate that the sanitizing composition is present in the air). In some embodiments, the sanitizing composition described herein does not include any additional glycol or any components other than triethylene glycol and water.

In some embodiments, the sanitizing composition described herein can include an additional glycol (e.g., propylene glycol (PG)) in an amount of from at least about 0.5% (e.g., at least about 1%, at least about 1.5%, at least about 2%, at least about 2.5%, at least about 3%, at least about 3.5%, at least about 4%, at least about 4.5%) by weight to at most about 99% (e.g., at most about 95%, at most about 90%, at most about 80%, at most about 70%, at most about 60%, at most about 50%, at most about 40%, at most about 30%, at most about 20%, at most about 10%, at most about 5%, at most about 4.5%, at most about 4%, at most about 3.5%, at most about 3%, at most about 2.5%, at most about 2%, at most about 1.5%, or at most about 1%) by weight of the composition.

In some embodiments, the sanitizing composition described herein can optionally include a material generally recognized as safe ("GRAS") as defined by the U.S. Food and Drug Administration. Examples of suitable GRAS materials include dimethyl ether, glycerin, chlorine dioxide, and hypochlorus acid.

In some embodiments, the sanitizing composition described herein can include (e.g., comprise, consist essentially of, or consist of) from about 50% to about 90% by weight triethylene glycol and from about 10% to about 50% by weight water. In some embodiments, the sanitizing composition described herein can include (e.g., comprise, consist essentially of, or consist of) (1) triethylene glycol in an amount of from about 52% to about 90% by weight of the composition; (2) water in an amount of from about 5% to about 48% by weight of the composition; and (3) propylene glycol in an amount of from about 0% to about 5% (e.g., from about 0.5% to about 5%) by weight of the composition. In some embodiments, the sanitizing composition described herein can include (e.g., comprise, consist essentially of, or consist of) about 52.5% by weight triethylene glycol, about 1% by weight propylene glycol, and about 46.5% by weight deionized water.

In some embodiments, this disclosure also features a method sanitizing a space (e.g., an indoor space). In some embodiments, the method can include applying (e.g., by dispersing, spraying, nebulizing, atomizing, or vaporizing) a composition containing triethylene glycol (e.g., a sanitizing composition described herein) into a space (e.g., an indoor space) containing a pathogen in an amount effective to inactivate (e.g., kill) the pathogen. In some embodiments, applying the sanitizing composition can be performed by a system that generates fog, smoke, or haze, such as a vaporizer (e.g., a smoke generator), a nebulizer (e.g., a scent dispersion unit), or an atomizer (e.g., a humidifier). The system can be those known in the art, such as the fog/haze machines or smoke simulators used in emergency training or used in the lighting industry to generate theatrical effects.

In some embodiments, the method can further include vaporizing the composition (e.g., in a humidifier, a fog/haze machine, or a smoke generator) before applying (e.g., spraying) the composition into a space. In some embodiments, vaporizing the composition can be performed by treating the composition with steam or heating. For example, when vaporizing the composition is performed by heating, the method can include delivering the composition to a heat exchanger to vaporize the composition. The heated vapor can be forced through a nozzle as vapor and/or liquid droplets (or liquid particles) to form a visible or invisible aerosol, fog, smoke, or haze. For example, when the sanitizing composition described herein is applied (e.g., dispersed or sprayed) into a space using a vaporizer, the vaporizer can have a liquid reservoir and can use an electric pump to propel the sanitizing composition in the liquid reservoir into a heat exchanger where the sanitizing composition is vaporized. The heated vapor is forced through a nozzle as vapor and as liquid droplets (or liquid particles) that form an opaque fog, smoke, haze, or visible or non-visible aerosol.

In some embodiments, when the composition is applied (e.g., dispersed or sprayed) into a space using an atomizer (e.g., a nebulizer), the composition can be converted to an aerosol by pressure. For example, the composition can be pumped into a series of specific sized chambers in an atomizer or nebulizer to increase the pressure and velocity of the composition in order to convert it from a liquid to an aerosol. In some embodiments, ultrasonic and/or vibrating mesh technology can be used to apply the composition into a space through an atomizer or a nebulizer.

In some embodiments, applying the composition can form vapor and/or liquid droplets (or liquid particles) that contain triethylene glycol. In some embodiments, the liquid droplets can form an aerosol that contains triethylene glycol. In some embodiments, applying the composition can form an aerosol, a vapor, or a mixture thereof. In some embodiments, the aerosol liquid droplets can have an average diameter of from at least about 10 nm (e.g., at least about 20 nm, at least about 50 nm, at least about 100 nm, at least about 200 nm, at least about 500 nm, at least about 1 μm, at least about 2 μm, or at least about 5 μm) to at most about 10 μm (e.g., at most about 8 μm, at most about 6 μm, at most about 5 μm, at most about 4 μm, at most about 2 μm, at most about 1 μm). In some embodiments, the method described herein can generate from at least about 2000 (e.g., at least about 3000, at least about 4000, at least about 5000, at least about 6000, at least about 8000, or at least about 10,000) to at most about 100,000 (e.g., at most about 50,000 or at most about 25,000) liquid droplets per $cm^3$ of the space (e.g., the indoor space).

In some embodiments, applying (e.g., dispersing or spraying) the composition can be performed intermittently (e.g., either at a constant interval or at irregular intervals). In some embodiments, when the composition is applied intermittently at a constant interval, the frequency of the application can vary as desired depending on factors such as the concentration of triethylene glycol in the composition, the temperature and humidity of the space, the size of the space, the desired concentration of the composition in the space, and the air exchange rates. In some embodiments, the preferred temperature of the space can range from about 5° C. to about 50° C. (e.g., from about 10° C. to about 30° C. or from about 15° C. to about 30° C.). In some embodiments, the preferred relative humidity of the space can range from about 5% to about 75% (e.g., from about 15% to about 70%, from about 30% to about 65%, or from about 45% to about 60%). In some embodiments, the time period between two applications of the composition can be from at least about 10 seconds (e.g., at least about 30 seconds, at least about 1 minute, at least about 1.5 minutes, at least about 2 minutes, at least about 5 minutes, at least about 10 minutes, at least about 30 minutes, or at least about 1 hour) to at most about 2 hours (e.g., at most about 1 hour, at most about 30 minutes, at most about 10 minutes, or at most about 5 minutes).

In some embodiments, the concertation of the sanitizing composition in an aerosol form (e.g., the concentration of the liquid droplets containing the sanitizing composition) in a space can be from at least about 0.01 $mg/m^3$ (e.g., at least about 0.02 $mg/m^3$, at least about 0.04 $mg/m^3$, at least about 0.05 $mg/m^3$, at least about 0.1 $mg/m^3$, at least about 0.2 $mg/m^3$, at least about 0.3 $mg/m^3$, at least about 0.4 $mg/m^3$, at least about 0.5 $mg/m^3$, at least about 0.6 $mg/m^3$, at least about 0.8 $mg/m^3$, at least about 1 $mg/m^3$, at least about 1.5 $mg/m^3$, at least about 2 $mg/m^3$, at least about 2.5 $mg/m^3$, at least about 3 $mg/m^3$, at least about 3.5 $mg/m^3$, at least about 4 $mg/m^3$, at least about 4.5 $mg/m^3$, or at least about 5 $mg/m^3$) or at most about 10 $mg/m^3$ (e.g., at most about 9 $mg/m^3$, at most about 8 $mg/m^3$, at most about 7 $mg/m^3$, at most about 6 $mg/m^3$, at most about 5 $mg/m^3$, at most about 4 $mg/m^3$, at most about 3 $mg/m^3$, at most about 2 $mg/m^3$, at most about 1 $mg/m^3$, at most about 0.7 $mg/m^3$, at most about 0.5 $mg/m^3$, or at most about 0.3 $mg/m^3$). For example, the concertation of the sanitizing composition in an aerosol form (e.g., the concentration of the liquid droplets containing the sanitizing composition) in a space can be from about 0.02 $mg/m^3$ to about 1.6 $mg/m^3$ (e.g., from about 0.04 $mg/m^3$ to about 1 $mg/m^3$).

In some embodiments, the total concentration of the TEG (including TEG in the aerosol and TEG in the vapor) or glycol (e.g., including both TEG and PG) in a space can be from at least about 0.01 $mg/m^3$ (e.g., at least about 0.02 $mg/m^3$, at least about 0.04 $mg/m^3$, at least about 0.05 $mg/m^3$, at least about 0.1 $mg/m^3$, at least about 0.2 $mg/m^3$, at least about 0.3 $mg/m^3$, at least about 0.4 $mg/m^3$, at least about 0.5 $mg/m^3$, at least about 0.6 $mg/m^3$, at least about 0.8 $mg/m^3$, at least about 1 $mg/m^3$, at least about 1.5 $mg/m^3$, at least about 2 $mg/m^3$, at least about 2.5 $mg/m^3$, at least about 3 $mg/m^3$, at least about 3.5 $mg/m^3$, at least about 4 $mg/m^3$, at least about 4.5 $mg/m^3$, or at least about 5 $mg/m^3$) or at most about 10 $mg/m^3$ (e.g., at most about 9 $mg/m^3$, at most about 8 $mg/m^3$, at most about 7 $mg/m^3$, at most about 6 $mg/m^3$, at most about 5 $mg/m^3$, at most about 4 $mg/m^3$, at most about 3 $mg/m^3$, at most about 2 $mg/m^3$, at most about 1 $mg/m^3$, at most about 0.8 $mg/m^3$, at most about 0.6 $mg/m^3$, at most about 0.5 $mg/m^3$, or at most about 0.3 $mg/m^3$). For example, the total concertation of the TEG (including TEG in the aerosol and TEG in the vapor) or glycol (including glycol in the aerosol and in the vapor) in a space can be from about 0.01 mg/m$^3$ to about 3 mg/m$^3$ (e.g., e.g., from about 0.5 mg/m$^3$ to about 3 mg/m$^3$ or from about 0.5 mg/m$^3$ to about 1 mg/m$^3$).

Without wishing to be bound by theory, it is believed that the sanitizing composition or the TEG having a concentration within the above ranges can effectively kill or inactivate at least 98% (e.g., at least 98.5%, at least 99%, at least 99.5, or at least 99.9%) of a pathogen in a space within a short period of time (e.g., at most 60 minutes, at most 30 minutes, at most 15 minutes, at most 10 minutes, at most 5 minutes, at most 3 minutes, at most 2 minutes, at most 1 minute, or at most 30 seconds). In some embodiments, at least about 0.5 gram (e.g., at least about 1 gram, at least about 2 grams, at least about 3 grams, or at least about 4 grams) and/or at most about 5 grams of the sanitizing composition can be used in a space having a volume of 1000 cubic feet every 4 hours (e.g., every two hours or every one hour).

In some embodiments, to practice the sanitizing method described herein in an indoor space, one can place a system described herein (e.g., a vaporizer or an atomizer such as a nebulizer) in the center or on one or more sides of the indoor space to be treated. In some embodiments, multiple systems can be used at appropriate places to ensure even distribution of the sanitizing composition. The sanitizing composition described herein can be applied from the system(s) into the indoor space until a desired sanitization (or disinfection) level is achieved. In some embodiments, the sanitizing composition can be applied intermittently (e.g., every 2 minutes or every 30 minutes) to maintain the desired sanitization level.

In some embodiments, the sanitizing composition described herein can be applied to an indoor space to be treated via an HVAC unit. For example, a system containing the composition described herein can be connected to the return plenum of an HVAC unit through a tubing. The composition can then be applied into the indoor space through the HVAC unit until a desired sanitization (or disinfection) level is achieved. This approach can sanitize both the filter in the HVAC unit and the indoor space.

In some embodiments, the space (e.g., the indoor space) to be treated can include a pathogen suspending in the air and the sanitizing method described herein is capable of inactivating (e.g., killing) the pathogen in the air. In some embodiments, the space can include a pathogen on a surface (e.g., either a hard or soft surface, or either a non-porous or a porous surface) and the sanitizing method described herein is capable of inactivating (e.g., killing) the pathogen on the surface. In some embodiments, the surface can be any surface in an indoor space, such as a surface of a wall, a floor, a desk, a chair, a computer, a rug, or a drape. Without wishing to be bound by theory, it is believed that triethylene glycol can adhere to the pathogen either in the air or on a surface to inactivate the pathogen by denaturing or disrupting the protein or membrane of the pathogen. Further, without wishing to be bound by theory, it is believed that, when the pathogen is a bacterium, a *Mycobacterium*, a mold, or a spore, the sanitizing composition described herein can inactivate the pathogen by desiccation.

In another aspect, this disclosure features a packaged product that includes a container (e.g., a can or a bottle), and the sanitizing composition described herein in the container. The packaged product can be either pressurized or non-pressurized.

The following examples are illustrative and not intended to be limiting.

EXAMPLES

General Procedure 1

Efficacy Study Using Time Controlled Release Application Against Pathogens with 10-Minute Sample Collection Time Test Substance:
Sanitizing Composition #1: triethylene glycol (52.25 wt %), propylene glycol (1 wt %), and DI water (46.75%)
Number of Samples: 3
Sampling Times/Exposure (Contact) Time: 0 min; 15 minutes, 30 minutes, 60 minutes and 90 minutes.
Test System:
Relative Humidity Range: 30-40%
Temperature Range: 23-25° C.
Materials Needed:
A closed, 16 cubic meter bioaerosol test chamber with negative pressure capabilities
Magnehelic differential pressure gauge
Calibrated mass flow meters
Collision 24-jet or similar multi-nozzle nebulizer
TSI AM520 aerosol monitor
Tryptic Soy Broth
Tryptic Soy Agar Culture Plates
Ace Glass Inc. Impingers (AGI-30)
200 µl MicroPipette+tips
1000 µl MicroPipette+tips
Sterile 1.5 mL microcentrifuge tubes
Sterile 50 mL conical tubes
Sterile 15 mL conical tubes
250 mL suspension culture flask with vent cap
Serological Pipette (25 mL)
Phosphate Buffered Saline Solution (PBS)
Vortex laboratory mixer
Centrifuge
Incubator
⅓ HP Gast Rotary Vane Vacuum Pump
Biological Safety Cabinet
TSI AM520
Dispersion Device (e.g., Aura Nebulizer or Clearify Vaporizer) for dispersing tested substance into test chamber.
Procedures
1a. Preparation of bacterial test microorganism with growth and incubation requirements.
  a. 250 mL of tryptic soy broth (30 g/L) containing the desired organism (e.g., a bacterium) was incubated overnight at 30-37° C.
  b. After incubation, flasks containing 250 mL of microorganism culture were prepared in tryptic soy broth media, and incubated for 24-48 hours at 30-37° C.
  c. Stock cultures were centrifuged for 10 minutes at 3000 rpm in an LD-3 centrifuge in sterile 15 mL conical tubes, growth media were removed, and the cells re-suspended in sterile PBS buffer for aerosolization.
  d. 100 µL was extracted from the organism stock and serially diluted in sterile PBS in 1.5 mL micro-centrifuge tubes, and then plated on tryptic soy agar plates and placed in the incubator for stock concentration determination.

e. Culture was streaked on tryptic soy agar plates to ensure no contamination was present prior to starting the trials.
f. Note: test working stocks were grown in sufficient volume to satisfy use quantities for all tests conducted using the same culture stock material.

1 b. Preparation of viral test microorganisms
 a. A host bacteria culture was prepared by combining 100 mL of the appropriate broth with 1.0E+09 cfu of host bacteria in a 250 mL vented culture flask.
 b. The shaker flask was placed on an orbital shaker table inside of the incubator at 30-37° C. set at 100 rotation/min. for 2 hours.
 c. Pure viral seed stock was removed from the freezer and allowed to thaw at room temperature for 20 minutes.
 d. After 2 hours, the shaker flask of bacteria was moved to the biosafety cabinet for infection.
 e. 1 mL of 1.0E+08 pfu/mL of the pathogen was added to the bacterial stock by pipette, then placed back in the incubator on the shaker table
 f. After 24 hours, the culture was removed from the shaker table and moved to a biosafety cabinet to be poured into 15 mL conical tubes.
 g. The conical tubes were placed into the centrifuge to be spun at 4000 rpm for 15 minutes.
 h. After the 15 minutes, the conical tubes were decanted into 15 mL conical tubes.
 i. A sample of the remaining stock was taken to determine concentration. Concentration was determined by serially diluting the stock, and plating the stock, and sticking the plates into the incubator.
  In order to plate the bacteriophages, the host bacterium was prepared on the previous day according to the preparation of bacterial test microorganism with growth and incubation requirements.
  The bacterial stock was diluted 1:9 into PBS before use in plating.
  800 uL of sterile PBS was aliquoted into 1.5 mL micro centrifuge tubes for plating. 100 μL of the bacterial 1:9 stock was added to each tube for plating.
  100 μL of the viral sample was added and serially diluted and plated on tryptic soy agar plates.
  After drying in the biosafety cabinets, the plates were placed in the incubator to grow over night.
 j. The concentration was determined the next day by counting the plaques in the bacterial lawn.

2. Formulation Bactericidal/Viral Challenge
 Prior to the bioaerosol testing, Sanitizing Composition #1 was tested in liquid form to ensure that all reduction yielded in the trial was due to the performance in the chamber and not because of killing occurring in the impinger fluid.
 a. The bactericidal challenge occurred at a range of 10× dilutions designed to provide a broad range of possible composition concentrations that could occur in an impinger sample. Sanitizing Composition #1 was diluted in sterile PBS.
  The concentrations of Sanitizing Composition #1 tested were: 0.0001%, 0.001%, 0.01%, 0.1%, and 1%.
 b. The desired organism was grown overnight according to the bacterial growth procedure prior to testing.
 c. A 100 μL sample of the organism was placed in normal PBS and allowed to sit for 10 minutes at room temperature in the biosafety cabinet. After 10 minutes, the sample was serially diluted and plated on a tryptic soy agar plate and placed in the incubator.
 d. Another 100 uL sample of the same organism was placed in PBS containing Sanitizing Composition #1 at one of the concentrations listed above. After a 10 minute contact time in the biosafety cabinet, the sample was diluted in normal PBS and plated on tryptic soy agar plates and placed in the incubator.
 e. The plates were counted and recorded in a lab notebook for analysis.
 f. The organism underwent testing with this procedure for each concentration of Sanitizing Composition #1 listed above.
 g. Each organism tested in the bioaerosol chamber underwent this testing to ensure that, if the results were within 10% of each other, Sanitizing Composition #1 was confirmed to not affect the microorganisms when in the PBS during sampling.

3. Determination of Sanitizing Composition #1 Concentration in Test Chamber
 a. The reservoir in the dispersion device (e.g., a nebulizer or a vaporizer) will be filled to the fill line with Sanitizing Composition #1 prior to every run.
 b. The dispersion device was turned on to the proper settings.
 c. The dispersion device was primed outside of the test chamber by actuating the dispersal button on the dispersion device for a minimum of five minutes.
 d. The dispersion device was then placed in the test chamber on a stainless-steel table in the middle of the chamber 3 feet above ground level.
 e. The TSI AM520 was placed in the test chamber 3 feet away from the dispersion device at the same height.
 f. The dispersion device was shut in the chamber and dispersed for a set amount of time. A mixing fan was run in the chamber to assure a homogenous mixture was achieved.
 g. After the dispersal, the chamber air was monitored by the TSI AM520 for the duration of the trial.
 h. At the end of the trial, the data was extracted from the TSI AM520 to determine the aerosol concentration throughout the trial.

4. Test system requirements and Bioaerosol Test Chamber set up
 a. Bioaerosol testing was conducted using a dynamically balanced bioaerosol test chamber with integrated decontamination systems.
 b. For air sampling, the chamber was equipped with four ⅜-inch diameter stainless steel probes that were positioned 18" from the nearest sidewall.
 c. Temperature and relative humidity were monitored throughout each trial by a remote sensor to ensure the following levels were maintained. The levels were recorded in the lab notebook at the beginning of each bioaerosol sample.
 Temperature range: 25° C.+/−3° C.
 Relative humidity range: 30-40%
 d. The reservoir of the dispersion device was filled with Sanitizing Composition #1 to the fill line on the reservoir before each trial.
 e. The dispersion device was turned on to the proper settings.
 f. The dispersion device was primed by setting the timer on the dispersion device to a specified setting and letting it run outside the test chamber for at least 5 minutes. This allowed the lines of the dispersion device to fill with Sanitizing Composition #1 and ready to be dispersed.

g. After priming, the dispersion device was placed in the center of the test chamber, 3 feet off of the ground on a stainless-steel table.
h. The dispersion device was turned on to the specified setting, determined through pre-testing, and allowed to pre-condition the chamber before the introduction of bioaerosol (i.e., pathogen aerosol) such that the aerosol containing Sanitizing Composition #1 was maintained at a concentration of about 0.04 mg/m$^3$ throughout the entire trial. This simulates a room with an already working unit having a bioaerosol introduced into it.
i. The Collison nebulizer was filled with approximately 40 mL of biological stock and operated at 40 psi for a period of 20 minutes. The nebulization stock for each trial was prepared according to the bacterial growth section of this protocol. Once the culture was resuspended in PBS, 100 μL of antifoam A was added to the stock to reduce the shearing of the bacteria observed during nebulization
j. The AGI-30 impingers was filled with 20 mL of sterilized PBS with an addition of 0.005% v/v Tween 80 for bioaerosol collection. The addition of Tween 80 was used in order to increase the impinger collection efficiency and de-agglomeration of all microorganisms.
k. The chamber mixing fan, located in the corner of the chamber under the dispersion device port pointing towards the far corner ceiling, was turned on for the duration of the trial to ensure that a homogenous mixture of bioaerosol was present throughout the chamber.

5. Sample collection
  a. The trial test for determining the efficacy of Sanitizing Composition #1 against a pathogen was performed as follows:
  (1) From a time period of −60 minute to −30 minute, the test chamber was dispersed with Sanitizing Composition #1 using a dispersion device to form aerosol particles until a relatively constant aerosol concentration (i.e., 0.04 mg/m$^3$) was reached. To maintain the aerosol concentration of Sanitizing Composition #1 in the chamber, the dispersion device was repeatedly turned on for 10 seconds and off for two minutes throughout the entire trial when the dispersion device was a vaporizer, and was repeatedly turned on for 55 seconds and off for one minute throughout the entire trial when the dispersion was a nebulizer.
  (2) From a time period of −30 minute to −10 minute, the test chamber was dispersed with a pathogen using a nebulizer to form pathogen aerosol particles until a desired pathogen aerosol concentration was reached.
  (3) From a time period of −10 minute to 0 minute, air sample in the test chamber was collected by using two AGI-30 impingers located at opposite corners of the chamber. The collection was performed for 10 minutes. The sample collected is known as T-0 sample.
  (4) From a time period of 0 minute to 15 minute, no sample collection was made.
  (5) From a time period of 15 minute to 25 minute, air sample in the chamber was collected for 10 minutes. The sample collected is known as T-15 sample.
  (6) From a time period of 25 minute to 30 minute, no sample collection was made.
  (7) From a time period of 30 minute to 40 minute, air sample in the chamber was collected for 10 minutes. The sample collected is known as T-30 sample.
  (8) From a time period of 40 to 60 minute, no sample collection was made.
  (9) From a time period of 60 minute to 70 minute, air sample in the chamber was collected for 10 minutes. The sample collected is known as T-60 sample.
  (10) From a time period of 70 to 90 minute, no sample collection was made.
  (11) From a time period of 90 minute to 100 minute, air sample in the chamber was collected for 10 minutes. The sample collected is known as T-90 sample.
  (12) In some tests, a T-120 sample was collected using the same procedure described above.
  b. The control test was performed in a manner similar to the trial test except that only a pathogen (but no Sanitizing Composition #1) was introduced into the test chamber. In the control test, the air sample was collected following the same schedule of the trial test.
  c. Collected impinger chamber samples were pooled and mixed at each sample interval for each test and placed in 15 mL conical tubes.
  d. The conical tubes containing the samples were immediately taken to a biosafety cabinet to be serially diluted in PBS and plated on tryptic soy agar plates.
  e. In between sampling, the impingers will be taken to the lab sink to be rinsed 6× with DI water and then dried prior to being used for the next sampling.
  f. Subsequent impinger samplings were taken at various time points throughout the trial as outlined above. These samples were enumerated for viable pathogen aerosol concentration to measure the effective viable bioaerosol reduction achieved during operation of the dispersion device dispersing Sanitizing Composition #1 over time.
  g. All samples were plated in triplicate on tryptic soy agar media over a minimum 3 log dilution range.
  h. Plates were incubated for 24-48 hours and enumerated for viable colony forming units (cfu) to calculate pathogen aerosol concentrations in the chamber and reduction of viable microorganisms.

6. Settling Test
  a. The settling test was conducted simultaneously during the chamber testing trials using glass slides. Three sterile ½"/2" blank glass slides were placed on a stainless-steel table in the middle of the test chamber.
  b. The blank slides accounted for settling of the bioaerosol during the trial.
  c. After the test, the chamber was evacuated for 20 minutes before a technician can enter. At this point the slides were removed from the chamber.
  d. These slides were placed in 50 mL conical tubes containing 10 mL of PBS buffer solution with Tween 80 for extraction.
  e. The conical tubes were closed and vigorously shaken and vortexed for 5 minutes prior to sampling.
  f. A sample was taken from each conical tube and serially diluted and plated to be enumerated.

7. Calculation of % Reduction
  a. To calculate the effect of Sanitizing Composition #1, the starting pathogen concentration of the trial was compared to the starting pathogen concentration of the control. The method for nebulization and stock remained the same so the difference in concentration will be attributed to the inhibition by Sanitizing Composition #1. All reduction calculations of the trials were compared to the starting concentration of the uninhibited control.

b. AGI-30 impinger collection calculation:

Viable pathogen aerosol concentration collection (Ca)= cfu/L or pfu/L of chamber air (cfu/L when the pathogen is a bacterium and pfu/L when the pathogen is a virus).

Viable pathogen Impinger concentration collection (CImp)=cfu or pfu/mL from enumeration of impinger sample.

Impinger sample collection volume (Ivol)=20 mL collection fluid/impinge.

AGI-30 impinger sample flow rate (Qimp)=12.5 L/min.

AGI-30 impinger sample time (t)=5 or 10 minutes, test dependent.

Vp is viable particles in cfu or pfu per liter of air.

For viable impinger aerosol concentration collection (Ca)=cfu/L or pfu/L of chamber air (cfu/L when the pathogen is a bacterium and pfu/L when the pathogen is a virus):

$$C_a = \frac{C_{Imp} \cdot I_{vol}}{Q_{imp}} t$$

The aerosol system viable delivery efficiency (expressed as %) is:

$$\text{Efficiency} = \frac{C_a}{V_p} \cdot 100$$

c. All triplicate runs were averaged to obtain a mean and standard deviation for each trial.

d. Total viable pathogen concentrations along with reductions over time (i.e., Log reductions of aerosolized pathogens) were calculated and graphed for each trial. In order to determine the log reduction of the trials over time, the percent of viable pathogen remaining in the chamber at each time point was compared to the initial concentration taken at time zero. This percentage value was then multiplied by the logarithmic function with a base number of 10 to give the values displayed.

e. The mean+/−standard deviation for each set of replicates was plotted in order to generate the effective log reduction for each organism versus operational time.

General Procedure 2

Efficacy Study Using Single Shot Application Against Pathogens

The single shot test was performed using the same materials and equipment as the time controlled release test described in General Procedure 1 except for the following differences:

a. In the single shot test, Sanitizing Composition #1 was only dispersed into the test chamber once for four seconds at the time point of 0 minute;

b. The dispersion device was a Nimbus vaporizer; and c. The single shot test was performed as follows:

(1) From a time period of −30 minute to −10 minute, the test chamber was dispersed with a pathogen using a nebulizer to form pathogen aerosol particles until a desired pathogen aerosol concentration was reached.

(2) From a time period of −10 minute to 0 minute, air sample in the test chamber was collected by using two AGI-30 impingers located at opposite corners of the chamber. The collection was performed for 10 minutes. The sample collected is known as T-0 sample.

(3) At the time point of 0 minute, Sanitizing Composition #1 was dispersed into the test chamber once for four seconds. From a time period of 0 minute to 0.5 minute, no sample collection was made.

(4) From a time period of 0.5 minute to 10.5 minute, air sample in the chamber was collected for 10 minutes. The sample collected is known as T-0.5 sample.

(5) From a time period of 10.5 minute to 15 minute, no sample collection was made.

(6) From a time period of 15 minute to 25 minute, air sample in the chamber was collected for 10 minutes. The sample collected is known as T-15 sample.

(7) From a time period of 25 minute to 60 minute, no sample collection was made.

(8) From a time period of 60 minute to 70 minute, air sample in the chamber was collected for 10 minutes. The sample collected is known as T-60 sample.

General Procedure 3

Efficacy Study Using Time Controlled Release Application Against Pathogens with 2-Minute Sample Collection Time The test was performed using the same materials and equipment as the time controlled release test described in General Procedure 1 except that the sample collection was reduced from 10 minutes to 2 minutes and that T-120, T-180, and T240 samples were collected using the same procedure described General Procedure 1.

General Procedure 4

Efficacy Study Using Single Shot Application Against Pathogens with 2-Minute Sample Collection Time The test was performed using the same materials and equipment as the single shot test described in General Procedure 2 except that the sample collection was reduced from 10 minutes to 2 minutes.

Example 1: Evaluation of Sanitizing Composition #1 for its Efficacy Against an *Mycobacterium smegmatis* in an Aerosol by Using a Nebulizer Sanitizing Composition #1 was tested against *Mycobacterium smegmatis* derived from ATCC 607 (which is a known surrogate for *Mycobacterium tuberculosis*) in an aerosol by using a nebulizer following General Procedure 1.

The test results for *Mycobacterium smegmatis* in the aerosol are summarized in Table 1. As used herein, "control concentration" refers to the concentration of a pathogen (i.e., *Mycobacterium smegmatis* in this Example) in a control experiment where no sanitizing composition was used, "trial concentration" refers to the concentration of a pathogen in a trial experiment where Sanitizing Composition #1 was used, and "net $Log_{10}$ reduction" is obtained by deducting control $Log_{10}$ reduction from $Log_{10}$ reduction. The values in Table 1 are averaged from three replicates.

TABLE 1

| Time (min) | Control Conc at time point (CFU/m$^3$) | Trial Conc at time point (CFU/m$^3$) | % reduction | LOG$_{10}$ Reduction | Control LOG$_{10}$ Reduction | Net LOG$_{10}$ Reduction |
|---|---|---|---|---|---|---|
| 0 | 6.04E+07 | 1.38E+07 | 77.206% | 0.64 | 0.00 | 0.64 |
| 15 | 4.05E+07 | 3.47E+04 | 99.943% | 3.24 | 0.17 | 3.07 |
| 30 | 1.56E+07 | 1.17E+04 | 99.981% | 3.71 | 0.59 | 3.12 |
| 60 | 7.36E+06 | 2.13E+03 | 99.996% | 4.45 | 0.91 | 3.54 |
| 90 | 3.80E+06 | 1.07E+02 | 99.9998% | 5.75 | 1.20 | 4.55 |

As shown in Table 1, Sanitizing Composition #1 unexpectedly exhibited average net Log$_{10}$ pathogen reduction of 3.07 and 4.55 after exposure times of 15-25 minutes and 90-100 minutes against *Mycobacterium smegmatis* in the aerosol, respectively. In other words, the composition was able to kill more than 99.9% of the *Mycobacterium smegmatis* in the aerosol in only 15-25 minutes. The above results suggest that Sanitizing Composition #1 would be effective in killing *Mycobacterium tuberculosis* in the aerosol form in a space.

In addition, the settling test showed that the average concentrations of *Mycobacterium smegmatis* settling on a glass slide were 1.67E+03 CFU/slide in the control experiment (where Sanitizing Composition #1 was not introduced into the test chamber) and below the detection limit of 6.67E+00 CFU/slide in the trial experiment (where Sanitizing Composition #1 was introduced into the test chamber), respectively. In other words, the results showed that Sanitizing Composition #1 was able to kill at least 99.40% (i.e., a Log$_{10}$ pathogen reduction of at least 2.22) *Mycobacterium smegmatis* in the air. The above results suggest that Sanitizing Composition #1 would be effective in killing *Mycobacterium tuberculosis* in the air.

Example 2: Evaluation of Sanitizing Composition #1 for its Efficacy Against *Salmonella* in an Aerosol by Using a Nebulizer Sanitizing Composition #1 was tested against *Salmonella typhimurium* derived from ATCC 53648 (which is a known surrogate for pathogenic *Salmonella* species such as *Salmonella enterica*, a gram-negative bacterium) in an aerosol by using a nebulizer following General Procedure 1.

The test results for *Salmonella typhimurium* in the aerosol are summarized in Table 2. The values in Table 2 are averaged from three replicates.

As shown in Table 2, Sanitizing Composition #1 unexpectedly exhibited average net Log$_{10}$ pathogen reduction of 2.35 and 3.46 after exposure times of 15-25 minutes and 30-40 minutes against *Salmonella typhimurium* in the aerosol, respectively. In other words, the composition was able to kill more than 99% of the *Salmonella typhimurium* in the aerosol in only 15-25 minutes. The above results suggest that Sanitizing Composition #1 would be effective in killing pathogenic *Salmonella* species such as *Salmonella enterica* in the aerosol form in a space.

In addition, the settling test showed that the average concentrations of *Salmonella typhimurium* settling on a glass slide were 5.66E+05 CFU/slide in the control experiment (where Sanitizing Composition #1 was not introduced into the test chamber) and 1.40E+05 CFU/slide in the trial experiment (where Sanitizing Composition #1 was introduced into the test chamber), respectively. In other words, the results showed that Sanitizing Composition #1 was able to kill 75.25% (i.e., a Log$_{10}$ pathogen reduction of 0.61) *Salmonella typhimurium* in the air. The above results suggest that Sanitizing Composition #1 would be effective in killing pathogenic *Salmonella* species such as *Salmonella enterica* in the air.

Example 3: Evaluation of Sanitizing Composition #1 for its Efficacy Against *Klebsiella* in an Aerosol by Using a Nebulizer Sanitizing Composition #1 was tested against *Klebsiella aerogenes* derived from ATCC 51697 (which is a known surrogate for pathogenic *Klebsiella* species such as *Klebsiella pneumoniae*, a gram-negative bacterium) in an aerosol by using a nebulizer following General Procedure 1.

The test results for *Klebsiella aerogenes* in the aerosol are summarized in Table 3. The values in Table 3 are averaged from three replicates.

TABLE 2

| Time (min) | Control Conc at time point (CFU/m$^3$) | Trial Conc at time point (CFU/m$^3$) | % reduction | LOG$_{10}$ Reduction | Control LOG$_{10}$ Reduction | Net LOG$_{10}$ Reduction |
|---|---|---|---|---|---|---|
| 0 | 5.60E+07 | 1.76E+07 | 68.571% | 0.50 | 0.00 | 0.50 |
| 15 | 1.33E+07 | 5.95E+04 | 99.894% | 2.97 | 0.62 | 2.35 |
| 30 | 6.45E+06 | 2.24E+03 | 99.996% | 4.40 | 0.94 | 3.46 |
| 60 | 1.81E+06 | 3.20E+02 | 99.999% | 5.24 | 1.49 | 3.75 |
| 90 | 9.49E+05 | 1.60E+02 | 100.000% | 5.54 | 1.77 | 3.77 |

TABLE 3

| Time (min) | Control Conc at time point (CFU/m³) | Trial Conc at time point (CFU/m³) | % reduction | LOG$_{10}$ Reduction | Control LOG$_{10}$ Reduction | Net LOG$_{10}$ Reduction |
|---|---|---|---|---|---|---|
| 0 | 1.20E+06 | 4.96E+05 | 58.758% | 0.38 | 0.00 | 0.38 |
| 15 | 4.03E+05 | 4.00E+03 | 99.667% | 2.48 | 0.48 | 2.00 |
| 30 | 2.96E+05 | 1.07E+03 | 99.911% | 3.05 | 0.61 | 2.44 |
| 60 | 1.76E+05 | 1.07E+02 | 99.991% | 4.05 | 0.83 | 3.22 |
| 90 | 1.41E+05 | 1.07E+02 | 99.991% | 4.05 | 0.93 | 3.12 |

As shown in Table 3, Sanitizing Composition #1 unexpectedly exhibited average net Log$_{10}$ pathogen reduction of 2.00 and 3.22 after exposure times of 15-25 minutes and 60-70 minutes against *Klebsiella aerogenes* in the aerosol, respectively. In other words, the composition was able to kill 99% of the *Klebsiella aerogenes* in the aerosol in only 15-25 minutes. The above results suggest that Sanitizing Composition #1 would be effective in killing pathogenic *Klebsiella* species such as *Klebsiella pneumoniae* in the aerosol form in a space.

In addition, the settling test showed that the average concentrations of *Klebsiella aerogenes* settling on a glass slide were 3.33E+03 CFU/slide in the control experiment (where Sanitizing Composition #1 was not introduced into the test chamber) and 4.44E+01 CFU/slide in the trial experiment (where Sanitizing Composition #1 was introduced into the test chamber), respectively. In other words, the results showed that Sanitizing Composition #1 was able to kill 98.67% (i.e., a Log$_{10}$ pathogen reduction of 1.88) *Klebsiella aerogenes* in the air. The above results suggest that Sanitizing Composition #1 would be effective in killing pathogenic *Klebsiella* species such as *Klebsiella pneumoniae* in the air.

Example 4: Evaluation of Sanitizing Composition #1 for its Efficacy Against *Pseudomonas* in an Aerosol by Using a Nebulizer Sanitizing Composition #1 was tested against *Pseudomonas fluorescens* derived from ATCC 21781 (which is a known surrogate for pathogenic *Pseudomonas* species such as *Pseudomonas aeruginosa*, a gram-negative bacterium) in an aerosol by using a nebulizer following General Procedure 1.

The test results for *Pseudomonas fluorescens* in the aerosol are summarized in Table 4. The values in Table 4 are averaged from three replicates.

As shown in Table 4, Sanitizing Composition #1 unexpectedly exhibited average net Log$_{10}$ pathogen reduction of 3.10 after an exposure time of 15-25 minutes against *Pseudomonas syringae* in the aerosol. In other words, the composition was able to kill more than 99.9% of the *Pseudomonas fluorescens* in the aerosol in only 15-25 minutes. The above results suggest that Sanitizing Composition #1 would be effective in killing pathogenic *Pseudomonas* species such as *Pseudomonas aeruginosa* in the aerosol form in a space.

In addition, the settling test showed that the average concentrations of *Pseudomonas fluorescens* settling on a glass slide were 7.25E+01 CFU/slide in the control experiment (where Sanitizing Composition #1 was not introduced into the test chamber) and 8.33E+00 CFU/slide in the trial experiment (where Sanitizing Composition #1 was introduced into the test chamber), respectively. In other words, the results showed that Sanitizing Composition #1 was able to kill 88.51% (i.e., a Log$_{10}$ pathogen reduction of 0.94) *Pseudomonas fluorescens* in the air. The above results suggest that Sanitizing Composition #1 would be effective in inactivating pathogenic *Pseudomonas* species such as *Pseudomonas aeruginosa* in the air.

Example 5: Evaluation of Sanitizing Composition #1 for its Efficacy Against *Aspergillus* in an Aerosol by Using a Vaporizer Sanitizing composition #1 was tested against the spores of *Aspergillus brasiliensis* (a mold) in an aerosol and by using a vaporizer following General Procedure 1.

The test results for the spores of *Aspergillus brasiliensis* in the aerosol are summarized in Table 5. The values in Table 5 are averaged from three replicates.

TABLE 4

| Time (min) | Control Conc at time point (CFU/m³) | Trial Conc at time point (CFU/m³) | % reduction | LOG$_{10}$ Reduction | Control LOG$_{10}$ Reduction | Net LOG$_{10}$ Reduction |
|---|---|---|---|---|---|---|
| 0 | 3.79E+05 | 9.92E+03 | 97.380% | 1.58 | 0.00 | 1.58 |
| 15 | 2.00E+05 | 1.60E+02 | 99.958% | 3.37 | 0.28 | 3.10 |
| 30 | 7.25E+04 | 1.07E+02 | 99.972% | 3.55 | 0.72 | 2.83 |
| 60 | 1.92E+04 | 1.07E+02 | 99.972% | 3.55 | 1.29 | 2.26 |
| 90 | 4.80E+03 | 4.00E+01 | 99.989% | 3.98 | 1.90 | 2.08 |

TABLE 5

| Time (min) | Control Conc at time point (CFU/m³) | Trial Conc at time point (CFU/m³) | % reduction | LOG$_{10}$ Reduction | Control LOG$_{10}$ Reduction | Net LOG$_{10}$ Reduction |
|---|---|---|---|---|---|---|
| 0 | 4.05E+07 | 2.72E+07 | 32.895% | 0.17 | 0.00 | 0.17 |
| 15 | 8.53E+06 | 1.39E+06 | 96.579% | 1.47 | 0.68 | 0.79 |
| 30 | 5.33E+06 | 2.03E+05 | 99.500% | 2.30 | 0.88 | 1.42 |
| 60 | 2.77E+06 | 8.72E+04 | 99.785% | 2.67 | 1.16 | 1.50 |
| 90 | 1.07E+06 | 7.15E+04 | 99.824% | 2.75 | 1.58 | 1.17 |

As shown in Table 5, Sanitizing Composition #1 unexpectedly exhibited average net Log$_{10}$ pathogen reduction of 1.42 after an exposure time of 30-40 minutes against the spores of *Aspergillus brasiliensis* in the aerosol. In other words, the composition was able to kill more than 95% of the spores of *Aspergillus brasiliensis* in the aerosol in only 30-40 minutes. The above results suggest that Sanitizing Composition #1 would be effective in killing mold spores in the aerosol form in a space.

In addition, the settling test showed that the average concentrations of *Aspergillus brasiliensis* settling on a glass slide were 1.41E+06 CFU/slide in the control experiment (where Sanitizing Composition #1 was not introduced into the test chamber) and 1.78E+03 CFU/slide in the trial experiment (where Sanitizing Composition #1 was introduced into the test chamber), respectively. In other words, the results showed that Sanitizing Composition #1 was able to kill 99.87% (i.e., a Log$_{10}$ pathogen reduction of 2.90) the spores of *Aspergillus brasiliensis* in the air. The above results suggest that Sanitizing Composition #1 would be effective in killing mold spores in the air.

Example 6: Evaluation of Sanitizing Composition #1 for its Efficacy Against *Listeria* in an Aerosol by Using a Nebulizer Sanitizing Composition #1 was tested against *Listeria innocua* derived from ATCC 33090 (which is a known surrogate for pathogenic *Listeria* species such as *Listeria Monocytogenes*, a gram-positive bacteria) in an aerosol by using a nebulizer following General Procedure 1.

The test results for *Listeria innocua* in the aerosol are summarized in Table 6. The values in Table 6 are averaged from three replicates.

As shown in Table 6, Sanitizing Composition #1 unexpectedly exhibited average net Log$_{10}$ pathogen reduction of 2.55 after an exposure time of 15-25 minutes against *Listeria innocua* in the aerosol. In other words, the composition was able to kill more than 99% of the *Listeria innocua* in the aerosol in only 15-25 minutes. The above results suggest that Sanitizing Composition #1 would be effective in killing pathogenic *Listeria* species such as *Listeria Monocytogenes* in the aerosol form in a space.

In addition, the settling test showed that the average concentrations of *Listeria innocua* settling on a glass slide were 7.67E+03 CFU/slide in the control experiment (where Sanitizing Composition #1 was not introduced into the test chamber) and 4.44E+01 CFU/slide in the trial experiment (where Sanitizing Composition #1 was introduced into the test chamber), respectively. In other words, the results showed that Sanitizing Composition #1 was able to kill 99.42% (i.e., a Log$_{10}$ pathogen reduction of 2.24) *Listeria innocua* in the air. The above results suggest that Sanitizing Composition #1 would be effective in killing pathogenic *Listeria* species such as *Listeria Monocytogenes* in the air.

Example 7: Evaluation of a Sanitizing Composition #1 for its Efficacy Against Staphylococcus in an Aerosol by Using a Nebulizer and a Vaporizer Sanitizing Composition #1 was tested against Methicillin resistant *Staphylococcus epidermidis* derived from ATCC 12228 (which is a known surrogate for MRSA) in an aerosol by using an Aura nebulizer and a Clearify vaporizer following General Procedure 1.

The test results for *Staphylococcus epidermidis* in the aerosol obtained from a nebulizer and a vaporizer are summarized in Tables 7 and 8, respectively. The values in Tables 7 and 8 are averaged from three replicates.

TABLE 6

| Time (min) | Control Conc at time point (CFU/m³) | Trial Conc at time point (CFU/m³) | % reduction | LOG$_{10}$ Reduction | Control LOG$_{10}$ Reduction | Net LOG$_{10}$ Reduction |
|---|---|---|---|---|---|---|
| 0 | 1.81E+07 | 2.88E+06 | 84.118% | 0.80 | 0.00 | 0.80 |
| 15 | 7.60E+06 | 2.13E+04 | 99.882% | 2.93 | 0.38 | 2.55 |
| 30 | 5.01E+06 | 3.04E+03 | 99.983% | 3.78 | 0.56 | 3.22 |
| 60 | 3.23E+06 | 1.92E+03 | 99.989% | 3.98 | 0.75 | 3.23 |
| 90 | 1.92E+06 | 6.40E+02 | 99.996% | 4.45 | 0.98 | 3.48 |

TABLE 7

Log$_{10}$ Reduction Obtained from an Aura Nebulizer

| Time (min) | Control Conc at time point (CFU/m$^3$) | Trial Conc at time point (CFU/m$^3$) | % reduction | LOG$_{10}$ Reduction | Control LOG$_{10}$ Reduction | Net LOG$_{10}$ Reduction |
|---|---|---|---|---|---|---|
| 0 | 2.45E+08 | 1.12E+07 | 95.43478% | 1.34 | 0.00 | 1.34 |
| 15 | 8.19E+07 | 4.27E+03 | 99.99826% | 4.76 | 0.48 | 4.28 |
| 30 | 3.04E+07 | 1.60E+03 | 99.99935% | 5.19 | 0.91 | 4.28 |
| 60 | 1.12E+07 | 3.20E+02 | 99.99987% | 5.88 | 1.34 | 4.54 |

TABLE 8

Log$_{10}$ Reduction Obtained from a Clearify Vaporizer

| Time (min) | Control Conc at time point (CFU/m$^3$) | Trial Conc at time point (CFU/m$^3$) | % reduction | LOG$_{10}$ Reduction | Control LOG$_{10}$ Reduction | Net LOG$_{10}$ Reduction |
|---|---|---|---|---|---|---|
| 0 | 2.45E+08 | 8.21E+07 | 66.5217% | 0.48 | 0.00 | 0.48 |
| 15 | 8.19E+07 | 1.44E+04 | 99.9941% | 4.23 | 0.48 | 3.75 |
| 30 | 3.04E+07 | 2.13E+03 | 99.9991% | 5.06 | 0.91 | 4.15 |
| 60 | 1.12E+07 | 1.60E+03 | 99.9993% | 5.19 | 1.34 | 3.85 |

As shown in Tables 7 and 8, Sanitizing Composition #1 unexpectedly exhibited average net Log$_{10}$ pathogen reduction of 4.28 and 3.75 after an exposure time of 15-25 minutes against *Staphylococcus epidermidis* in the aerosol by using a nebulizer and a vaporizer, respectively. In other words, the composition was able to kill at least 99.9% of *Staphylococcus epidermidis* in the aerosol in only 15-25 minutes. The above results suggest that Sanitizing Composition #1 would be effective in killing MRSA in the aerosol form in a space. In addition, the results show that a nebulizer and a vaporizer are both effective in applying Sanitizing Composition #1 for killing MRSA in the aerosol.

In addition, the settling test showed that the average concentrations of *Staphylococcus epidermidis* settling on a glass slide were 1.41E+05 CFU/slide in the control experiment (where Sanitizing Composition #1 was not introduced into the test chamber) and 9.11E+03 CFU/slide in the trial experiment (where Sanitizing Composition #1 was introduced into the test chamber), respectively. In other words, the results showed that Sanitizing Composition #1 was able to kill 93.54% (i.e., a Log$_{10}$ pathogen reduction of 1.19) *Staphylococcus epidermidis* in the air. The above results suggest that Sanitizing Composition #1 would be effective in killing MRSA in the air.

Example 8: Evaluation of Sanitizing Composition #1 for its Efficacy Against Phi 6 in an Aerosol by Using a Nebulizer Sanitizing Composition #1 was tested against *Pseudomonas* virus Phi 6 derived from ATCC 21781-B1 in an aerosol by using a nebulizer following General Procedure 1. *Pseudomonas* virus Phi 6 is an enveloped double stranded RNA virus and is a known surrogate for other enveloped viruses including coronaviruses.

The test results for *Pseudomonas* virus Phi 6 in the aerosol are summarized in Table 9. The values in Table 9 are averaged from three replicates.

TABLE 9

| Time (min) | Control Conc at time point (PFU/m$^3$) | Trial Conc at time point (PFU/m$^3$) | % reduction | LOG$_{10}$ Reduction | Control LOG$_{10}$ Reduction | Net LOG$_{10}$ Reduction |
|---|---|---|---|---|---|---|
| 0 | 6.40E+05 | 1.60E+04 | 97.500% | 1.60 | 0.00 | 1.60 |
| 15 | 9.60E+04 | 5.33E+02 | 99.917% | 3.08 | 0.82 | 2.26 |
| 30 | 2.67E+04 | 5.33E+02 | 99.917% | 3.08 | 1.38 | 1.70 |
| 60 | 1.28E+04 | 1.07E+02 | 99.983% | 3.78 | 1.70 | 2.08 |
| 90 | 8.00E+03 | 1.07E+02 | 99.983% | 3.78 | 1.90 | 1.88 |

As shown in Table 9, Sanitizing Composition #1 unexpectedly exhibited average net Log$_{10}$ pathogen reduction of 2.26 after an exposure time of 15-25 minutes against *Pseudomonas* virus Phi 6 in the aerosol. In other words, the composition was able to inactivate more than 99% of *Pseudomonas* virus Phi 6 in the aerosol in only 15-25 minutes. The above results suggest that Sanitizing Composition #1 would be effective in inactivating enveloped viruses in the aerosol form in a space.

In addition, the settling test showed that the average concentrations of Phi 6 settling on a glass slide were 3.00E+02 PFU/slide in the control experiment (where Sanitizing Composition #1 was not introduced into the test chamber) and 4.44E+01 PFU/slide in the trial experiment (where Sanitizing Composition #1 was introduced into the test chamber), respectively. In other words, the results showed that Sanitizing Composition #1 was able to inactivate 85.19% (i.e., a $Log_{10}$ pathogen reduction of 0.83) Phi 6 in the air. The above results suggest that Sanitizing Composition #1 would be effective in inactivating enveloped viruses in the air.

Example 9: Evaluation of Sanitizing Composition #1 for its Efficacy Against MS2 in an Aerosol by Using a Nebulizer Sanitizing Composition #1 was tested against *Escherichia* virus MS2/Bacteriophage MS2 (MS2) derived from ATCC 15597-B1 in an aerosol by using a nebulizer following General Procedure 1. MS2 is a non-enveloped ssRNA virus that is generally harder to inactivate than enveloped viruses and is a known surrogate for influenza and SARS-CoV-2.

The test results for MS2 in the aerosol are summarized in Table 10. The values in Table 10 are averaged from three replicates.

TABLE 10

| Time (min) | Control Conc at time point (PFU/m$^3$) | Trial Conc at time point (PFU/m$^3$) | % reduction | $LOG_{10}$ Reduction | Control $LOG_{10}$ Reduction | Net $LOG_{10}$ Reduction |
|---|---|---|---|---|---|---|
| 0 | 1.87E+10 | 4.16E+08 | 97.7714% | 1.65 | 0.00 | 1.65 |
| 15 | 7.31E+09 | 1.81E+07 | 99.9029% | 3.01 | 0.41 | 2.61 |
| 30 | 4.19E+09 | 4.37E+06 | 99.9766% | 3.63 | 0.65 | 2.98 |
| 60 | 2.00E+09 | 1.81E+06 | 99.9903% | 4.01 | 0.97 | 3.04 |
| 90 | 1.47E+09 | 7.15E+05 | 99.9962% | 4.42 | 1.10 | 3.31 |
| 120 | 5.55E+08 | 2.85E+05 | 99.9985% | 4.82 | 1.53 | 3.29 |

As shown in Table 10, Sanitizing Composition #1 unexpectedly exhibited average net $Log_{10}$ pathogen reduction of 2.61 after an exposure time of 15-25 minutes against MS2 in the aerosol. In other words, the composition was able to inactivate more than 99% of MS2 in the aerosol in only 15-25 minutes. The above results suggest that Sanitizing Composition #1 would be effective in inactivating influenza and SARS-CoV-2 in the aerosol form in a space.

In addition, the settling test showed that the average concentrations of MS2 settling on a glass slide were 3.90E+07 PFU/slide in the control experiment (where Sanitizing Composition #1 was not introduced into the test chamber) and 8.22E+03 PFU/slide in the trial experiment (where Sanitizing Composition #1 was introduced into the test chamber), respectively. In other words, the results showed that Sanitizing Composition #1 was able to inactivate 99.98% (i.e., a $Log_{10}$ pathogen reduction of 3.68) MS2 in the air. The above results suggest that Sanitizing Composition #1 would be effective in inactivating influenza and SARS-CoV-2 in the air.

Example 10: Evaluation of the Efficacy of Single Shot of Sanitizing Composition #1 Against MS2 in an Aerosol by Using a Vaporizer Sanitizing Composition #1 was tested against *Escherichia* virus MS2/Bacteriophage MS2 (MS2) derived from ATCC 15597-B1 in an aerosol by using a Nimbus vaporizer following General Procedure 2. The test results are summarized in Table 11. The values in Table 11 are averaged from three replicates.

TABLE 11

| Time (min) | Control Conc at time point (PFU/m$^3$) | Trial Conc at time point (PFU/m$^3$) | % reduction | $LOG_{10}$ Reduction | Control $LOG_{10}$ Reduction | Net $LOG_{10}$ Reduction |
|---|---|---|---|---|---|---|
| 0 | 6.67E+10 | 4.27E+10 | N/A | N/A | N/A | N/A |
| 0.5 | 4.59E+10 | 6.16E+07 | 99.856% | 2.84 | 0.16 | 2.68 |
| 15 | 1.49E+10 | 6.24E+06 | 99.985% | 3.83 | 0.65 | 3.19 |
| 60 | 3.87E+09 | 2.64E+06 | 99.994% | 4.21 | 1.24 | 2.97 |

As shown in Table 11, Sanitizing Composition #1 unexpectedly exhibited average net Log 10 pathogen reduction of 2.68 and 3.19 after an exposure time of 0.5-10.5 minutes and 15-25 minutes against MS2 in the aerosol, respectively. In other words, the composition was able to inactivate more than 99% of MS2 in the aerosol in a single shot in only 0.5-10.5 minute. The above results suggest that Sanitizing Composition #1 would be effective in inactivating influenza and SARS-CoV-2 in the aerosol form in a single shot in a space.

Example 11: Evaluation of the Efficacy of Sanitizing Composition #1 Against MS2 in an Aerosol with a 2-Minute Sample Collection Time by Using a Nebulizer and a Vaporizer Sanitizing Composition #1 was tested against *Escherichia* virus MS2/Bacteriophage MS2 (MS2) derived from ATCC 15597-B1 in an aerosol by using an Aura Nebulizer and a Clearify vaporizer following General Procedure 3. The test results are summarized in Tables 12 and 13. The values in Tables 12 and 13 are averaged from three replicates.

As shown in Tables 12 and 13, Sanitizing Composition #1 unexpectedly exhibited average net $Log_{10}$ pathogen reduction of 1.23 and 2.07 after an exposure time of 2 minutes against MS2 in the aerosol by using a nebulizer and a vaporizer, respectively. In other words, the composition was able to inactivate at least 94% or 99% of MS2 in the aerosol in only 2 minutes. The above results suggest that Sanitizing Composition #1 would be effective in inactivating influenza and SARS-CoV-2 in the aerosol form in a short period of time (e.g., 2 minutes). In addition, the results show that a nebulizer and a vaporizer are both effective in applying Sanitizing Composition #1 for inactivating influenza and SARS-CoV-2 in the aerosol in a short period of time.

Example 12: Evaluation of the Efficacy of Single Shot of Sanitizing Composition #1 Against MS2 in an Aerosol with a 2-Minute Sample Collection Time by Using a Vaporizer Sanitizing Composition #1 was tested against *Escherichia* virus MS2/Bacteriophage MS2 (MS2) derived from ATCC 15597-B1 in an aerosol by using a Nimbus vaporizer following General Procedure 4. The test results are summarized in Table 14. The values in Table 14 are averaged from three replicates.

TABLE 12

$Log_{10}$ Reduction Obtained from an Aura Nebulizer

| Time (min) | Control Conc at time point ($PFU/m^3$) | Trial Conc at time point ($PFU/m^3$) | % reduction | $LOG_{10}$ Reduction | Control $LOG_{10}$ Reduction | Net $LOG_{10}$ Reduction |
|---|---|---|---|---|---|---|
| 0 | 5.33E+10 | 3.12E+09 | 94.1500% | 1.23 | 0.00 | 1.23 |
| 15 | 1.49E+10 | 1.21E+09 | 99.7400% | 1.65 | 0.55 | 1.09 |
| 30 | 1.12E+10 | 4.80E+05 | 99.9991% | 5.05 | 0.68 | 4.37 |
| 60 | 3.87E+09 | 3.20E+05 | 99.9994% | 5.22 | 1.14 | 4.08 |
| 90 | 1.49E+09 | 2.32E+05 | 99.9996% | 5.36 | 1.55 | 3.81 |
| 120 | 1.09E+09 | 1.28E+05 | 99.9998% | 5.62 | 1.69 | 3.93 |
| 180 | 4.61E+08 | 1.17E+04 | 100.0000% | 6.66 | 2.06 | 4.59 |
| 240 | 1.44E+08 | 9.60E+03 | 100.0000% | 6.74 | 2.57 | 4.18 |

TABLE 13

$Log_{10}$ Reduction Obtained from a Clearify Vaporizer

| Time (min) | Control Conc at time point ($PFU/m^3$) | Trial Conc at time point ($PFU/m^3$) | % reduction | $LOG_{10}$ Reduction | Control $LOG_{10}$ Reduction | Net $LOG_{10}$ Reduction |
|---|---|---|---|---|---|---|
| 0 | 4.07E+08 | 3.47E+06 | 99.1475% | 2.07 | 0.00 | 2.07 |
| 15 | 1.34E+08 | 1.07E+06 | 99.7377% | 2.58 | 0.48 | 2.10 |
| 30 | 7.89E+07 | 9.20E+05 | 99.7738% | 2.65 | 0.71 | 1.93 |
| 60 | 4.96E+07 | 5.41E+05 | 99.8669% | 2.88 | 0.91 | 1.96 |
| 90 | 3.25E+07 | 1.55E+05 | 99.9620% | 3.42 | 1.10 | 2.32 |
| 120 | 7.60E+06 | 1.95E+04 | 99.9952% | 4.32 | 1.73 | 2.59 |
| 180 | 2.91E+06 | 2.13E+03 | 99.9995% | 5.28 | 2.15 | 3.13 |
| 240 | 4.59E+05 | 1.07E+03 | 99.9997% | 5.58 | 2.95 | 2.63 |

TABLE 14

| Time (min) | Control Conc at time point (PFU/m$^3$) | Trial Conc at time point (PFU/m$^3$) | % reduction | LOG$_{10}$ Reduction | Control LOG$_{10}$ Reduction | Net LOG$_{10}$ Reduction |
|---|---|---|---|---|---|---|
| 0 | 6.67E+10 | 4.27E+10 | N/A | N/A | N/A | N/A |
| 0.5 | 4.59E+10 | 6.16E+07 | 99.856% | 2.84 | 0.16 | 2.68 |
| 15 | 1.49E+10 | 6.24E+06 | 99.985% | 3.83 | 0.65 | 3.19 |
| 60 | 3.87E+09 | 2.64E+06 | 99.994% | 4.21 | 1.24 | 2.97 |

As shown in Table 14, Sanitizing Composition #1 unexpectedly exhibited average net Log 10 pathogen reduction of 2.68 after an exposure time of 0.5-2.5 minute against MS2 in the aerosol. In other words, the composition was able to inactivate more than 99.8% of MS2 in the aerosol in a single shot in only 0.5-2.5 minute. The above results suggest that Sanitizing Composition #1 would be effective in inactivating influenza and SARS-CoV-2 in the aerosol form in a single shot in a space.

Other embodiments are in the following claims.

What is claimed is:

1. A method for sanitizing a space, comprising:
applying a composition comprising triethylene glycol into a space containing a pathogen in an amount effective to inactivate the pathogen;
wherein the pathogen comprises a *Staphylococcus*, a *Pseudomonas*, a *Listeria*, a *Salmonella*, a *Klebsiella*, a *Mycobacterium*, a mold, or a spore and the triethylene glycol is in the space at a concentration of from about 0.01 mg/m$^3$ to about 10 mg/m$^3$.

2. The method of claim 1, wherein the pathogen comprises Methicillin-resistant *Staphylococcus aureus* (MRSA), *Aspergillus brasiliensis*, *Pseudomonas aeruginosa*, *Listeria monocytogenes*, *Salmonella enterica*, or *Klebsiella pneumoniae*.

3. The method of claim 1, wherein the pathogen comprises *Mycobacterium tuberculosis*.

4. The method of claim 1, wherein the pathogen comprises an anthrax spore, a *Clostridium difficile* spore, or a mold spore.

5. The method of claim 1, wherein the triethylene glycol is in an amount of from about 10% to about 90% by weight of the composition.

6. The method of claim 1, wherein the composition further comprises water.

7. The method of claim 6, wherein the water is in an amount of from about 5% to about 90% by weight of the composition.

8. The method of claim 1, wherein the composition further comprises propylene glycol.

9. The method of claim 8, wherein the propylene glycol is in an amount of from about 0.5% to about 20% by weight of the composition.

10. The method of claim 1, wherein the composition comprises from about 50% to about 90% by weight triethylene glycol, and from about 10% to about 50% by weight water.

11. The method of claim 1, wherein the composition comprises about 52.5% by weight triethylene glycol, about 1% by weight propylene glycol, and about 46.5% by weight water.

12. The method of claim 1, wherein the triethylene glycol is in the space at a concentration of from about 0.01 mg/m$^3$ to about 1 mg/m$^3$.

13. The method of claim 1, wherein applying the composition forms an aerosol, a vapor, or a mixture thereof.

14. The method of claim 13, wherein the aerosol comprises liquid droplets having an average diameter of from about 10 nm to about 10 μm.

15. The method of claim 13, wherein the aerosol comprises liquid droplets and the aerosol is in the space at a concentration of from about 0.01 mg/m$^3$ to about 10 mg/m$^3$.

16. The method of claim 1, further comprising vaporizing the composition before applying the composition.

17. The method of claim 16, wherein vaporizing the composition is performed by treating the composition with steam or heating.

18. The method of claim 1, wherein the space comprises the pathogen suspending in the air and the method is capable of inactivating the pathogen in the air.

19. The method of claim 1, wherein the space comprises the pathogen on a surface and the method is capable of inactivating the pathogen on the surface.

20. The method of claim 1, wherein the space is an indoor space.

21. The method of claim 1, wherein the method is performed by an atomizer or a vaporizer.

22. The method of claim 1, wherein the composition is capable of inactivating at least 98% of the pathogen in the space within two minutes.

23. The method of claim 1, wherein the composition consist of triethylene glycol, water, and optionally propylene glycol.

24. The method of claim 1, wherein the pathogen is a mold or a mold spore.

25. The method of claim 1, wherein the space is occupied by human being.

* * * * *